(12) United States Patent
Korenweitz

(10) Patent No.: US 8,504,143 B2
(45) Date of Patent: Aug. 6, 2013

(54) METHOD AND SYSTEM FOR MEASURING HEART RATE VARIABILITY

(75) Inventor: Elyasaf Korenweitz, Elon-Moreh (IL)

(73) Assignee: Vitalcare Medical Ltd., Jerusalem (IL)

( * ) Notice: Subject to any disclaimer, the term of this patent is extended or adjusted under 35 U.S.C. 154(b) by 0 days.

(21) Appl. No.: 13/139,300

(22) PCT Filed: Dec. 15, 2009

(86) PCT No.: PCT/IL2009/001189
§ 371 (c)(1),
(2), (4) Date: Aug. 7, 2011

(87) PCT Pub. No.: WO2010/070640
PCT Pub. Date: Jun. 24, 2010

(65) Prior Publication Data
US 2012/0041326 A1   Feb. 16, 2012

Related U.S. Application Data

(60) Provisional application No. 61/193,674, filed on Dec. 15, 2008.

(51) Int. Cl.
*A61B 5/02* (2006.01)
*A61B 5/04* (2006.01)

(52) U.S. Cl.
USPC .......................................... 600/509; 600/508

(58) Field of Classification Search
USPC ................................. 600/508, 509
See application file for complete search history.

(56) References Cited

U.S. PATENT DOCUMENTS

| 5,285,793 | A | * | 2/1994 | Slovut et al. ................. 600/519 |
|---|---|---|---|---|
| 6,496,722 | B1 | | 12/2002 | Schmidt |
| 6,532,382 | B2 | | 3/2003 | Meier et al. |
| 6,731,794 | B2 | | 5/2004 | Zhang et al. |
| 7,200,528 | B2 | | 4/2007 | Schmidt et al. |
| 2002/0065473 | A1 | | 5/2002 | Wang et al. |
| 2005/0010116 | A1 | | 1/2005 | Korhonen et al. |
| 2005/0137482 | A1 | | 6/2005 | Laitio et al. |
| 2008/0275518 | A1 | | 11/2008 | Ghanem et al. |
| 2009/0292180 | A1 | | 11/2009 | Mirow |

OTHER PUBLICATIONS

International Application PCT/IL2009/001189 Search Report dated Apr. 22, 2010.
ECG Databases, http://www.physionet.org/physiobank/database/#ecg, Jul. 7, 2008.

(Continued)

*Primary Examiner* — George Evanisko
*Assistant Examiner* — Lindsey G Hankins
(74) *Attorney, Agent, or Firm* — D. Kligler I.P. Services Ltd.

(57) ABSTRACT

The invention provides a method and system for analyzing an ECG signal to diagnose a heart condition of an individual. A sequence $HB_i$ of consecutive heart beat durations in an ECG signal is obtained. One or more first parameters are calculated in a calculation involving pairs of $HB_i$ and $HB_{i-m}$, where m is a first predetermined integer and $HB_{i-m}$ is the duration of the heart beat that occurred m heart beats before the ith heart beat. One or more second parameters are calculated in a calculation involving pairs of $HB_i$ and $HB_{Bi-n}$, where n is second predetermined integer different from m. A diagnostic parameter is then calculated using the plurality of first parameters and the plurality of second parameters. The diagnostic parameter is compared to a predetermined threshold, and a diagnosis is made based on the comparison.

17 Claims, 4 Drawing Sheets

OTHER PUBLICATIONS

International Application # PCT/IB2011/051114 filed on Mar. 17, 2011.

Goldberger et al., "Fractal dynamics in Physiology: Alterations with Disease and Aging," Proceedings of the National Academy of Sciences, vol. 99, suppl.1, pp. 2466-2472, Feb. 19, 2002.

Acharya et al., "Heart Rate Analysis in Normal Subjects of Various Age Groups," Biomedical Engineering Online, vol. 3, issue 24, Jul. 20, 2004.

Tan et al., "Fractal Properties of Human Heart Period Variability: Physiological and Methodological Implications," Journal of Physiology, vol. 587, issue15, pp. 3929-394, Aug. 2009.

Porta et al., "Multimodal Signal Processing for the Analysis of Cardiovascular Variability," Philosophical Transactions of the Royal Society A: Mathematical, Physical and Engineering Sciences, vol. 367, pp. 391-409, Oct. 22, 2008.

Khaled et al., "Employing Time-Domain Methods and Poincaré Plot of Heart Rate Variability Signals to Detect Congestive Heart Failure," BIME Journal, vol. 6, issue 1, pp. 35-41, Dec. 2006.

Bauer et al., "Improved Stratification of Autonomic Regulation for risk prediction in post-infarction patients with preserved left ventricular function (ISAR-Risk)", European Heart Journal, vol. 30, pp. 576-583, year 2009.

Ghatak et al., "Lagged Poincaré and auto-correlation analysis of Heart rate variability in diabetes, Department of Physics and Meteorology, School of Medical Science and Technology", Indian Institute of Technology, May 28, 2010.

Lerma et al., "Poincare' plot indexes of heart rate variability capture dynamic adaptations after haemodialysis in chronic renal failure patients", Clinical Physiology and Functional Imaging Journal, vol. 23, pp. 72-80, year 2003.

International Application PCT/IB2011/051114 Search Report dated Oct. 17, 2011.

International Application PCT/IL2009/001189 International Preliminary Report on Patentability dated Jun. 21, 2001.

* cited by examiner (Beginning)

(End)

METHOD AND SYSTEM FOR MEASURING HEART RATE VARIABILITY

FIELD OF THE INVENTION

The present invention relates to a system and method for measuring heart rate variability (HRV).

BACKGROUND OF THE INVENTION

The rate at which a human heart beats is controlled by a feedback loop provided by a neurohumoral mechanism, the basic component of which is the autonomic nervous system, i.e. the sympathetic and parasympathetic nervous system. Heart rate variability is often decreased in severe ischaemic heart disease, congestive heart failure, ageing and diabetic neuropathy. Decreased HRV has been used as a tool in the early identification to of patients with severe ischaemic heart disease and severe heart failure who are at high risk of sudden death.

The electrocardiograph (ECG) signal is indicative of electrical currents in the heart muscle. The ECG signal of a single heart beat can be divided into several components. The P wave represents the spread of an impulse through the atria just before atrial contraction. This is followed by a QRS complex reflecting the spread of an impulse through the ventricles just before they contract. Currents generated as the ventricles recover appear in the ECG as a T wave. The time between consecutive R peaks, known as the RR interval, is normally used as a basis for heart rate measurements because the R peaks are relatively easy to detect.

The Poincaré plot is a scatter plot of current RR interval plotted against the previous RR interval, i.e. the ith RR interval in the series, RRi, is plotted as a function of the previous RR interval of the series, $RR_{i-1}$. The Poincaré plot thus consists of points of the form ($RR_i$, $RR_{i-1}$). The Poincaré is based on the observation that the length of a heartbeat is significantly determined by the length of the previous heart beat. When the variation in RR intervals over time is small, the plot will consist primarily of a relatively dense cluster of points. When the variation in the RR intervals is significant, the points of the plot will be scattered. The Poincaré plot thus provides a graphical representation of the RR data, which facilitates evaluation of HRV.

The Poincaré plot has been generalized to the so-called "m-lagged Poincaré plots" in which RR; is plotted as a function of $RR_{i-m}$, where m is an integer that may be greater than 1. It has been observed that the length of a heartbeat can affect several subsequent heartbeats.

U.S. Pat. No. 6,731,974 to Levitan et al discloses measuring heart rate variability by assigning a unit mass to each point in a Poincaré plot, and calculating the product of the quadrupole moments of the two axes of the plot.

U.S. Pat. No. 6,532,382 to Meier et al discloses calculating heart rate variability from an ECG signal by measuring discrete measuring values representative of the heart rate variability, and evaluating the Fourier transform of the measuring values.

SUMMARY OF THE INVENTION

The present invention provides a system and method for diagnosis of heart disease in an individual by analyzing an ECG signal of the individual. A sequence $HB_i$ of heartbeat durations is extracted from the ECG signal, where $HB_i$ is a duration of the ith heartbeat in the sequence. HBi may be obtained, for example, as the ith RR interval in the ECG. In accordance with the invention, two sequences of lagged heartbeat durations are constructed, ($HB_i$, $HB_{i-m}$) and ($HB_i$, $HB_{i-n}$), where m and n are two different positive integers. One or more parameters are calculated based on an analysis of the two sequences. A diagnostic parameter is then calculated in a calculation involving these parameters. The diagnostic parameter is then compared to a predetermined threshold and a diagnosis of the individual is made based on the comparison.

In one embodiment, the calculated parameters include $$xm_i = \frac{\sqrt{2}}{2}HB_i + \frac{\sqrt{2}}{2}HB_{i-m}, \; y_{mi} = -\frac{\sqrt{2}}{2}HB_i + \frac{\sqrt{2}}{2}HB_{i-m},$$

$$xn_i = \frac{\sqrt{2}}{2}HB_i + \frac{\sqrt{2}}{2}HB_{i-n}, \text{ and } yn_i = -\frac{\sqrt{2}}{2}HB_i + \frac{\sqrt{2}}{2}HB_{i-n}.$$

The diagnostic parameter is then calculated in a calculation involving the standard deviation $sd_{mx}$ of $x_{mi}$, the standard deviation $sd_{my}$ of $y_{mi}$, the standard deviation of the series $x_{ni}$, $sd_{nx}$ and the standard deviation of $y_{ni}$, $sd_{ny}$. For example, the diagnostic parameter may be equal to $$\frac{sd_{mx}}{sd_{my}} - \frac{sd_{nx}}{sd_{ny}}.$$

The inventors have found, for example, that using n=1 and m=10 a threshold of about 2 can be used to distinguish healthy individuals from individuals with heart disease.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Thus, in one of its aspects, the present invention provides a method for analyzing an ECG signal to diagnose a heart condition of an individual, comprising:

(a) generating a sequence HBi of consecutive heart beat durations in the ECG signal, where HBi is the duration of the ith heart beat in the sequence;

(b) for a plurality of integers i:
  (i) calculating one or more first parameters in a calculation involving $HB_i$ and $HB_{i-m}$, where m is a first predetermined integer and $HB_{i-m}$ is the duration of the heart beat that occurred m heart beats before the ith heart beat; and
  (ii) calculating one or more second parameters in a calculation involving $HB_i$ and $HB_{i-n}$, where n is second predetermined integer different from m;

(c) calculating a diagnostic parameter in a calculation involving the plurality of first parameters and the plurality of second parameters calculated in step (b), and (d) comparing the diagnostic parameter to a predetermined threshold, and making a diagnosis based on the comparison.

In another of its aspects, the invention provides a system for analyzing an ECG signal to diagnose a heart condition of an individual, comprising:

(a) an ECG device configured to generate an ECg signal of the individual;

(b) a processor configured to:

(i) Extract a sequence HBi of consecutive heart beat durations in the ECG signal, where HBi is the duration of the ith heart beat in the sequence;

(ii) for a plurality of integers i:

calculating one or more first parameters in a calculation involving $HB_i$ and $HB_{i-m}$, where m is a first predetermined integer and $HB_{i-m}$ is the duration of the heart beat that occurred m heart beats before the ith heart beat; and calculating one or more second parameters in a calculation involving $HB_i$ and $HB_{i-n}$, where n is second predetermined integer different from m;

(c) calculating a diagnostic parameter in a calculation involving the plurality of first parameters and the plurality of second parameters calculated in step (b), and (d) comparing the diagnostic parameter to a predetermined threshold, and displaying the result of the comparison on a display device.

The invention also provides a computer program comprising computer program code means for performing all the steps of the method of the invention when said program is run on a computer.

The invention further provides a computer program embodied on a computer readable medium.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
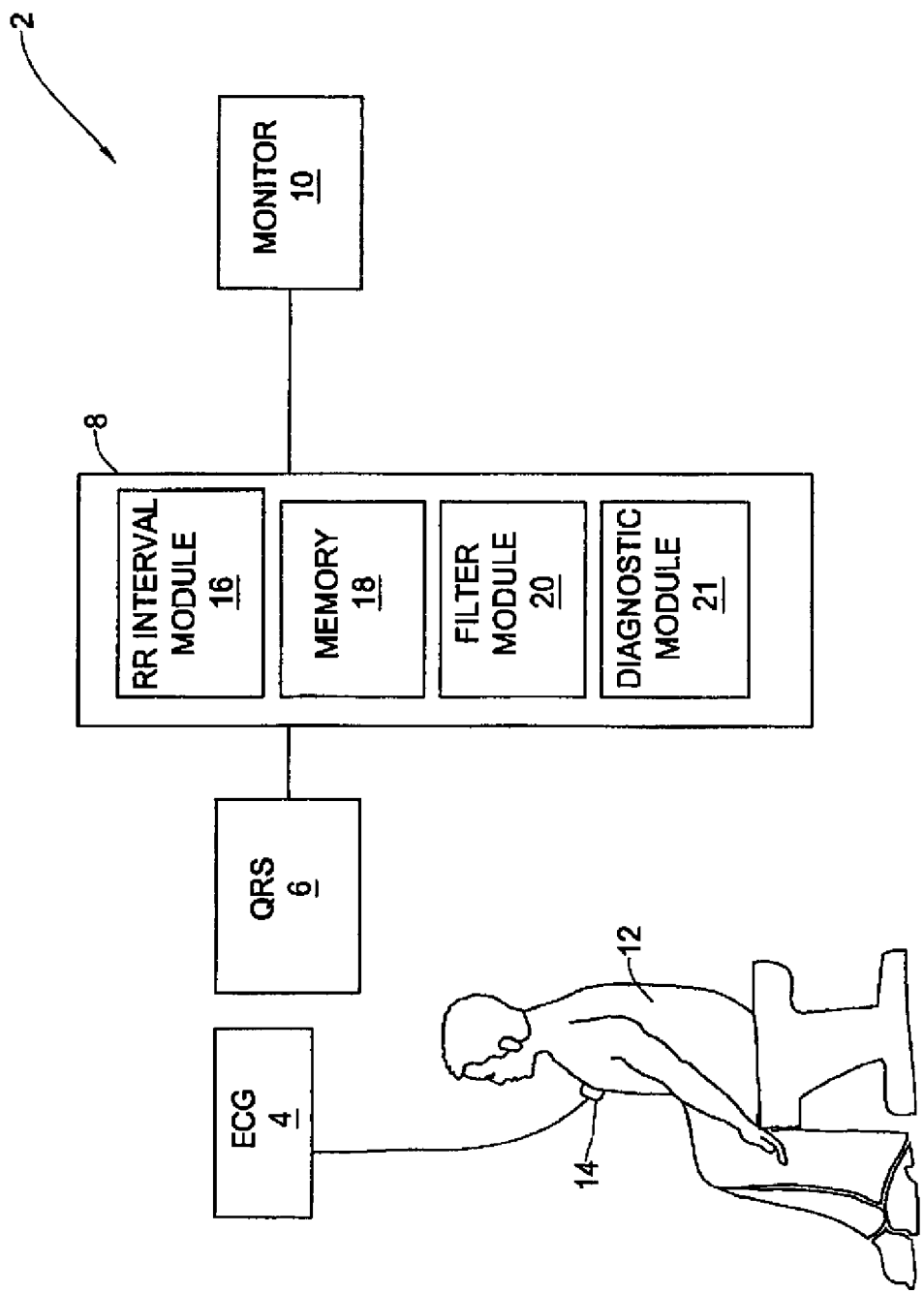
FIG. 1 shows a system for measuring heart rate variability in accordance with one embodiment of the invention.

FIG. 1 shows a system 2 for measuring HRV of an individual 12 in accordance with one embodiment of the invention. The system 2 comprises an ECG machine 4, a QRS detector 6, and a processing system 8 having a visual display device 10. An individual 12 is connected to the ECG machine 4 via leads 14. The output of the ECG machine 4 is input to the QRS detector 6 which detects the R peaks of the signals generated by the ECG machine 4 and inputs a voltage pulse to the processing system 8 for each detected R peak. The processing system 8 includes an RR interval module 16 which calculates from the arrival times of the pulses from the QRS detector 6 the time between consecutive pulses which are stored in a data file for the individual 12 in a memory 18. The file thus comprises a series $RR_i$, where is an integer, and $RR_i$ is the duration of the $i^{th}$ RR interval.

Once the RR interval data file for the individual 12 has been completed after monitoring the individual's heart rate for a predetermined period of time, for example 60 minutes, a filter module 20 filters the time series $RR_i$ in order to remove random noise from the $RR_i$ series, as explained below. The filtered $RR_i$ series is then input to a diagnostic module 21, which generates one or more diagnostic parameters of the RRi series that may be used to diagnose a condition of the individual 12. The RRi series, the filtered RRi series, or the results of any processing of the $RR_i$ series may be displayed on the visual display device 10.

Figure 2:
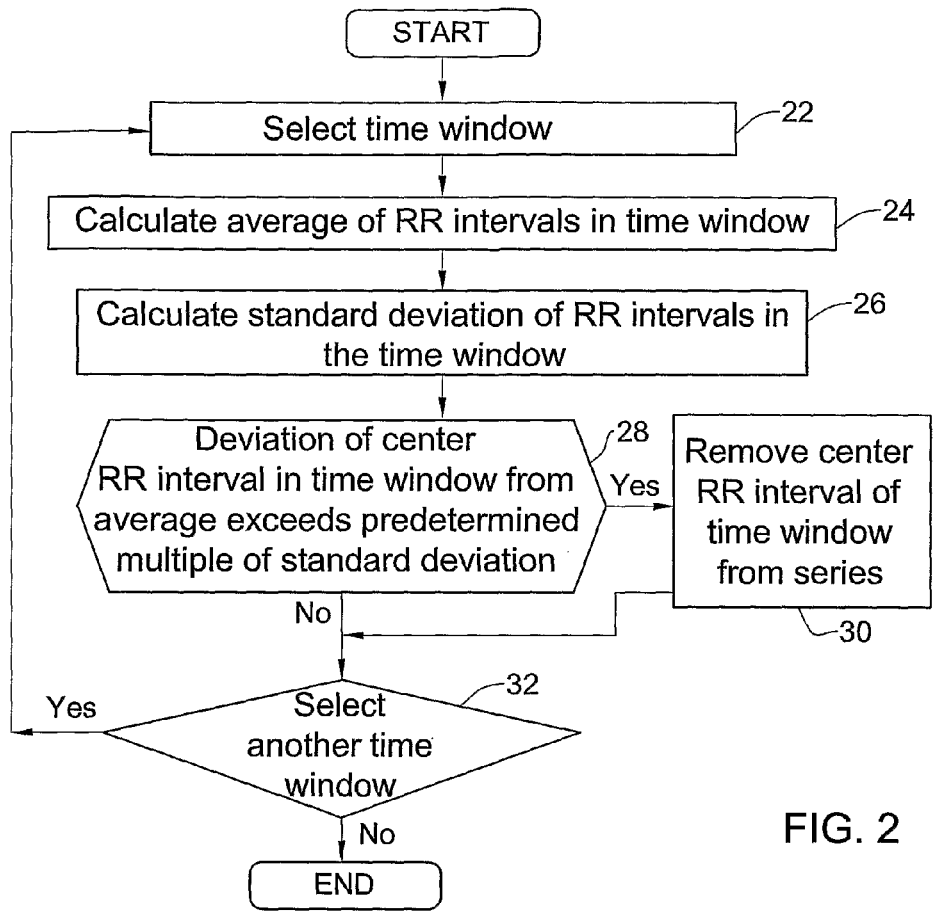
FIG. 2 shows a method for filtering an RRi sequence.

FIG. 2 shows a flow chart for a method of filtering the RRi series by the filter module 20, in accordance with one embodiment of the invention. In step 22, a time window is selected. The time window typically consists of a predetermined integer N of consecutive RR intervals in the series. N may be, for example, 65. The first time window selected will typically consist of the first N RR intervals in the series. In step 24, the average of the RR intervals in the selected time window is calculated, and in step 26 the standard deviation of the RR intervals in the time window is calculated. In step 28 it is determined whether the RR interval in the center of the time window deviates from the average by more than a predetermined multiple of the standard deviation. For example, it may be determined whether the center RR interval deviates from the average by more than 5 times the standard deviation. If yes, then in step 30, the RR interval in the center of the time window is removed from the RR series. The process then continues with step 30 where it is determined whether a new time interval is to be selected. If yes, then the process returns to step 22 with the selection of a new time interval. Typically, the next time window to be selected is obtained by shifting the current time window forward by one RR interval. Removing RR intervals from the RR series tends to remove random noise from the RR series. If in step 32 it is determined that a new time window is not to be selected, then the process ends.

Figure 3:
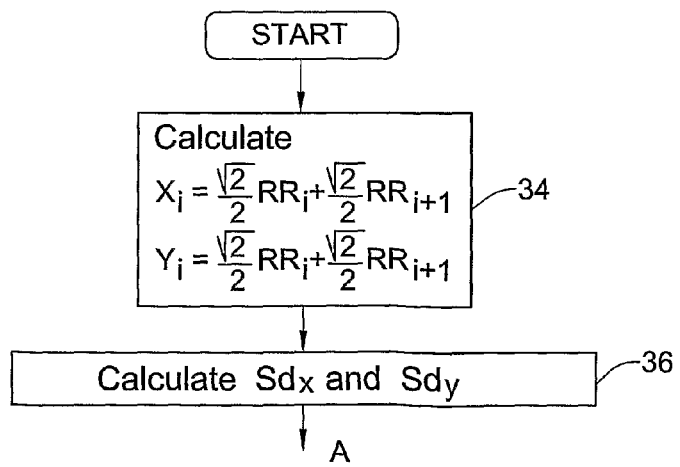
FIG. 3 shows a flow chart of a method for measuring heart rate variability in accordance with one embodiment of the invention.
Figure 3:
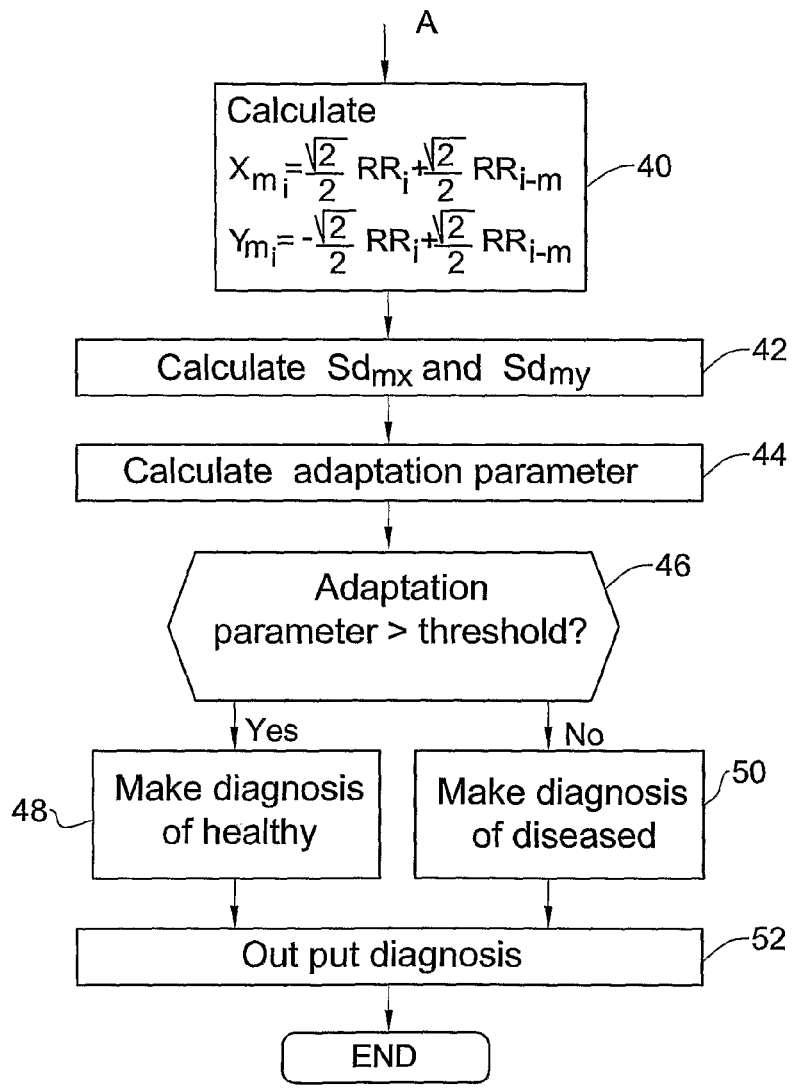

FIG. 3 shows a flow chart for a process of generating diagnosis parameters by the diagnostic module 21, in accordance with one embodiment of the invention. In step 34 two time series, $x_{mi}$ and $y_{mi}$, are calculated, where:

$$xm_i = \frac{\sqrt{2}}{2}RR_i + \frac{\sqrt{2}}{2}RR_{i-m}$$

$$y_{mi} = -\frac{\sqrt{2}}{2}RR_i + \frac{\sqrt{2}}{2}RR_{i-m}$$

where m is a first predetermined integer.

The pairs $(x_{mi}, y_{mi})$ are thus obtained by rotating the Poincaré plot counterclockwise by 45°. The standard deviation of the series $x_{mi}$ and $y_{mi}$, $sd_{ms}$ and $sd_{my}$ respectively, are then calculated in step 36.

In step 40 two new time series $x_{ni}$ and $y_{ni}$ are calculated, where;

$$xn_i = \frac{\sqrt{2}}{2}RR_i + \frac{\sqrt{2}}{2}RR_{i-n}$$

$$yn_i = -\frac{\sqrt{2}}{2}RR_i + \frac{\sqrt{2}}{2}RR_{i-n}$$

wherein n is a second predetermined positive integer different from m.

The standard deviation of the series $x_{ni}$ and $y_{ni}$, $sd_{nx}$ and $sd_{ny}$ respectively, are then calculated in step 42.

In step 44 a diagnostic parameter is calculated by the algebraic expression:

$$\frac{sd_{mx}}{sd_{my}} - \frac{sd_{nx}}{sd_{ny}} \qquad (1)$$

In step 46 it is determined whether the diagnostic parameter is greater than a predetermined threshold. The predetermined threshold may be, for example, 2. If yes, then in step 48 a diagnosis is made that the individual is healthy. If no, then in step 50, a diagnosis of diseased is made. The diagnosis is output in step 52 to one or both of the memory 18 or the display 10, and the process terminates.

EXAMPLES

ECG signals of 547 heart disease patients and 71 healthy individuals were downloaded from http://www.physionet.or and analyzed by the method of the invention.

Figure 4:
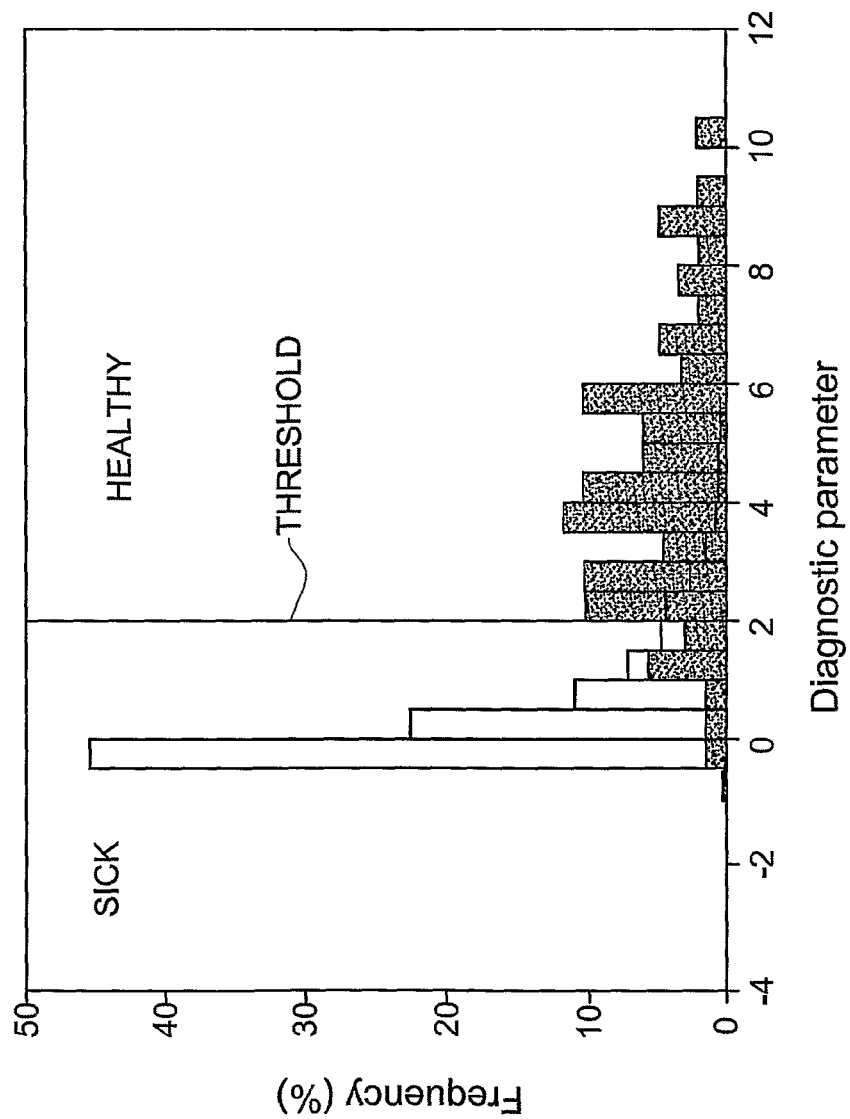
FIG. 4 shows a frequency distribution of the diagnostic parameter for healthy individuals (filled bars) and the heart disease patients (empty bars) using values of n=1 and m=10 and a threshold of 2.

FIG. 4 shows a frequency distribution of the diagnostic parameter for the healthy individuals (filled bars) and the heart disease patients (empty bars) calculated using Equation 1 above with of n=1 and m=10. It was found that the healthy individuals have values of this diagnostic parameter that are statistically significantly higher than those of the heart disease patients. The results show that a threshold of about 2 for this diagnostic parameter can be used to reliably distinguish between healthy and diseased individuals.

The invention claimed is:

1. A method for analyzing an ECG signal to diagnose a heart condition of an individual, comprising:
   (a) generating a sequence $HB_i$ of consecutive heart beat durations in the ECG signal, where $HB_i$ is the duration of the ith heart beat in the sequence;
   (b) for a plurality of integers i:
      (i) calculating one or more first parameters in a calculation involving $HB_i$ and $HB_{i-m}$, where m is a first predetermined integer and $HB_{i-m}$ is the duration of the heart beat that occurred m heart beats before the ith heart beat,
      wherein the first parameter is one or both of $$x_{mi} = \frac{\sqrt{2}}{2}HB_i + \frac{\sqrt{2}}{2}HB_{i-m}$$

and $$y_{mi} = -\frac{\sqrt{2}}{2}HB_i + \frac{\sqrt{2}}{2}HB_{i-m}.$$

and
   (ii) calculating one or more second parameters in a calculation involving $HB_i$ and $HB_{i-n}$, where n is second predetermined integer different from m;
   (c) calculating a diagnostic parameter in a calculation involving the first parameters and the second parameters calculated in step (b), and
   (d) comparing the diagnostic parameter to a predetermined threshold, and making a diagnosis based on the comparison.

2. The method according to claim 1 wherein the second parameter is one or both of $$x_{ni} = \frac{\sqrt{2}}{2}HB_i + \frac{\sqrt{2}}{2}HB_{i-n} \text{ and } y_{ni} = -\frac{\sqrt{2}}{2}HB_i + \frac{\sqrt{2}}{2}HB_{i-n}.$$

3. The method according to claim 2, wherein the diagnostic parameter is calculated in a calculation involving the standard deviation $sd_{mx}$ of $x_{mi}$, the standard deviation $sd_{my}$ of $y_{mi}$, the standard deviation of the series $x_{ni}$, $sd_{nx}$ and the standard deviation of $y_{ni}$, $sd_{ny}$.

4. The method according to claim 3 wherein the diagnostic parameter is equal to $$\frac{sd_{mx}}{sd_{my}} - \frac{sd_{nx}}{sd_{ny}}.$$

5. The method according to claim 1, wherein n=1.

6. The method according to claim 1, further comprising filtering random noise from the $HB_i$ sequence.

7. The method according to claim 1, wherein the sequence $HB_i$ is a sequence of time intervals between consecutive R peaks in the ECG signal.

8. The method according to claim 1, wherein m=10.

9. A system for analyzing an ECG signal to diagnose a heart condition of an individual, comprising:
   (a) an ECG device configured to generate an ECG signal of the individual; and
   (b) a processor configured to:
      (i) Extract a sequence $HB_i$ of consecutive heart beat durations in the ECG signal, where $HB_i$ is the duration of the ith heart beat in the sequence;
      (ii) for a plurality of integers i, perform the steps of:
      calculating one or more first parameters in a calculation involving $HB_i$ and $HB_{i-m}$, where m is a first predetermined integer and $HB_{i-m}$ is the duration of the heart beat that occurred m heart beats before the ith heart beat,
      wherein the first parameter is one or both of $$x_{mi} = \frac{\sqrt{2}}{2}HB_i + \frac{\sqrt{2}}{2}HB_{i-m} \text{ and } y_{mi} = -\frac{\sqrt{2}}{2}HB_i + \frac{\sqrt{2}}{2}HB_{i-m}.$$

and
      calculating one or more second parameters in a calculation involving $HB_i$ and $HB_{i-n}$, where n is second predetermined integer different from m;
      (iii) calculate a diagnostic parameter in a calculation involving the first parameters and the second parameters, and
      (iv) compare the diagnostic parameter to a predetermined threshold, and display the result of the comparison on a display device.

10. The system according to claim 9 wherein the second parameter is one or both of $$x_{ni} = \frac{\sqrt{2}}{2}HB_i + \frac{\sqrt{2}}{2}HB_{i-n} \text{ and } y_{ni} = -\frac{\sqrt{2}}{2}HB_i + \frac{\sqrt{2}}{2}HB_{i-n}.$$

11. The system according to claim 10 wherein the processor is configured to calculate the diagnostic parameter in a calculation involving the standard deviation $sd_{mx}$ of $x_{mi}$, the standard deviation $sd_{my}$ of $y_{mi}$, the standard deviation of the series $x_{ni}$, $sd_{nx}$ and the standard deviation of $y_{ni}$, $sd_{ny}$.

12. The system according to claim 11 wherein the processor is configured to calculate the diagnostic parameter using the algebraic expression $$\frac{sd_{mx}}{sd_{my}} - \frac{sd_{nx}}{sd_{ny}}.$$

13. The system according to claim 9 wherein n=1.

14. The system according to claim 9 further comprising filtering random noise from the $HB_i$ sequence.

15. The system according to claim 9 wherein the sequence $HB_i$ is a sequence of time intervals between consecutive R peaks in the ECG signal.

16. The system according to claim 9 wherein m=10.

17. A computer program embodied on a non-transitory computer readable medium comprising computer program code means for performing the following steps when said program is run on a computer:
   (a) generating a sequence $HB_i$ of consecutive heart beat durations in the ECG signal, where $HB_i$ is the duration of the ith heart beat in the sequence;
   (b) for a plurality of integers i:
      (i) calculating one or more first parameters in a calculation involving $HB_i$ and $HB_{i-m}$, where m is a first predetermined integer and $HB_{i-m}$ is the duration of the heart beat that occurred m heart beats before the ith heart beat, wherein the first parameter is one or both of $$x_{mi} = \frac{\sqrt{2}}{2} HB_i + \frac{\sqrt{2}}{2} HB_{i-m} \quad \text{and} \quad y_{mi} = -\frac{\sqrt{2}}{2} HB_i + \frac{\sqrt{2}}{2} HB_{i-m};$$

and
      (ii) calculating one or more second parameters in a calculation involving $HB_i$ and $HB_{i-n}$, where n is second predetermined integer different from m;
   (c) calculating a diagnostic parameter in a calculation involving the first parameters and the second parameters calculated in step (b), and
   (d) comparing the diagnostic parameter to a predetermined threshold, and making a diagnosis based on the comparison.

* * * * *